United States Patent [19]

Childs

[11] 4,440,963

[45] Apr. 3, 1984

[54] PRODUCTION OF MTBE AND ETBE

[75] Inventor: William V. Childs, Bartlesville, Okla.

[73] Assignee: Phillips Petroleum Company, Bartlesville, Okla.

[21] Appl. No.: 406,154

[22] Filed: Aug. 9, 1982

[51] Int. Cl.$^3$ .................. C07C 41/05; C07C 41/38
[52] U.S. Cl. ............................ 568/697; 568/699; 203/67; 203/70
[58] Field of Search .............. 568/697, 699; 203/67, 203/70

[56] References Cited

U.S. PATENT DOCUMENTS

| | | |
|---|---|---|
| 2,480,940 | 9/1949 | Leum . |
| 2,880,144 | 3/1959 | Bush . |
| 2,999,816 | 9/1961 | Bennett et al. . |
| 3,119,766 | 1/1964 | Voltz . |
| 3,846,088 | 11/1974 | Brown et al. . |
| 3,940,450 | 2/1976 | Lee . |
| 3,979,461 | 9/1976 | Ancillotti et al. . |
| 4,039,590 | 8/1977 | Ancillotti et al. . |
| 4,144,138 | 3/1979 | Rau et al. . |
| 4,198,530 | 4/1980 | Wentzheimer et al. . |
| 4,207,076 | 6/1980 | Bove et al. . |
| 4,299,999 | 11/1981 | Miktenko et al. .......... 568/697 |

FOREIGN PATENT DOCUMENTS 883081 11/1980 Belgium .

OTHER PUBLICATIONS

Horsely Aziotropic Data III, Advances in Chemistry Series 116 American Chemical Society 1973, p. 81.
Obenaus et al., The New and Versatile Huls–Process to Produce the Octane Improving MTB, AICHE (Philadelphia 1978).
Hydrocarbon Processing pp. 109–113, Dec. 1979.
Oil & Gas Journal, pp. 149–152, Apr. 19, 1979.

Primary Examiner—Howard T. Mars

[57] ABSTRACT

The fractionation of the methanol- or ethanol-containing methyl-(or ethyl)-tertiary-butyl ether reactor effluent is improved by employing 2-methylpentane to azeotrope methanol or ethanol overhead, or by using 1,1,3-trichloro-1,2,2-trifluoroethane (F113) to azeotrope methanol overhead, leaving a substantially pure MTBE or ETBE bottoms.

12 Claims, 1 Drawing Figure

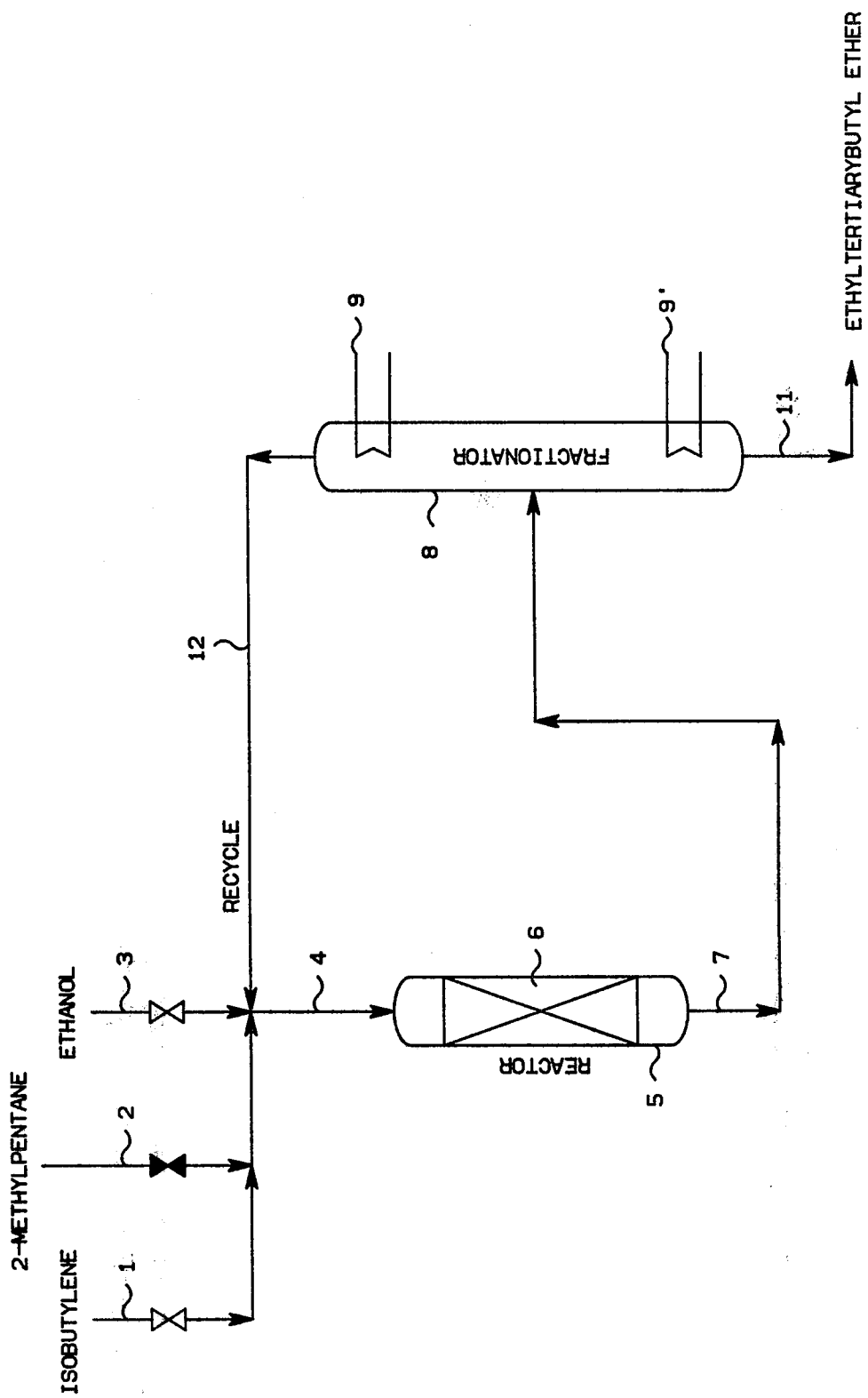

PRODUCTION OF MTBE AND ETBE

FIELD OF THE INVENTION

The invention in one aspect pertains to a process for the production of ethyl-tertiary-butyl ether (ETBE). The invention also is related to a process utilizing 2-methylpentane to fractionate ethanol from an ETBE reaction product stream. Further, the invention pertains to a method to recover ethanol for recycle to the ETBE reactor.

In another aspect, the invention pertains to a process for the production of methyl-tertiary-butyl ether (MTBE). This aspect also relates to a process utilizing either 2-methylpentane (TMP) or 1,1,2-trichloro-1,2,2-trifluoroethane (F113) to fractionate methanol from the MTBE reaction product stream. In another aspect, the invention pertains to a method to recover methanol for recycle to the reactor.

BACKGROUND OF THE INVENTION

Ethyl-tertiary-butyl ether (ETBE) is recognized as a suitable blending cosolvent for hydrous ethanol in gasoline stocks. See U.S. Pat. No. 4,207,076 (June 10, 1980). ETBE is blended into a fuel gasoline at about a 10 to 20 volume percent level, more usually about 9 to 12 percent, in which the fuel comprises about 70 to 84 percent gasoline and 5 to 20 percent of 95 percent ethanol (grain alcohol). ETBE solubilizes grain alcohol in gasoline in all proportions thereby allowing a wide latitude in the precise amount of ethanol which can be blended with the gasoline. In addition the presence of ETBE in the blend considerably increases its octane rating, both motor and research.

Methyl-tertiary-butyl ether (MTBE) is a recognized blending stock for raising the octane number of gasoline. MTBE, blended into gasoline at about a 10 to 20 volume percent level, increases both motor and research octane numbers by several units. The Environmental Protection Agency has sanctioned the use of MTBE in concentrations up to about 7 liquid volume percent in the United States.

ETBE and MTBE are produced by reacting isobutylene with either ethanol or methanol, resulting respectively in the formation of ETBE or MTBE. The reaction normally is conducted in liquid phase with relatively mild conditions. While mixed butylenes streams can be employed, only the tertiary olefin, isobutylene, reacts at the conditions employed. The isobutylene can be obtained from various sources, such as naphtha cracking, catalytic cracking, etc. Refer *Hydrocarbon Processing*, Dec., 1979, pages 109 and following, and *The Oil and Gas Journal*, Apr. 9, 1979, pages 149 and following.

The resulting reaction product stream contains the desired MTBE or ETBE, as well as unreacted isobutylene and methanol or ethanol. A problem that persists has been the separation of the unreacted alcohol from the MTBE or MTBE product. At equilibrium conversion, considerable alcohol remains in the reactor effluent, is difficult to remove by simple distillation, and may form troublesome azeotropes with ETBE and MTBE.

BRIEF DESCRIPTION OF THE INVENTION

In accordance with my invention, 2-methylpentane (TMP) is added to the ETBE reaction to assist in effecting recovery of substantially ethanol-free ETBE as bottoms product. The TMP azeotroping agent can be added before the isobutene/ethanol reaction step, since it passes therethrough unchanged, or added subsequent thereto and prior to product stream fractionation. The ethanol/TMP azeotropic overhead stream from the fractionation is recycled to the ethanol/isobutene reaction step.

In the aspect of my invention for improved recovery of MTBE, the process is similar to that described above for ETBE, except that as azeotroping agent either 2-methylpentane (TMP) or 1,1,2-trichloro-1,2,2-trifluoroethane (F113) is added to the system, either prior to the reaction step forming the MTBE or subsequent thereto but prior to the MTBE reactor effluent fractionation step. In fractionation of the MTBE reactor effluent, TMP or F113 takes methanol overhead as an azeotrope, leaving substantially pure MTBE as a bottoms stream. The TMP or F113 recycles, and needs to be added to the system only as needed to augment minor losses.

BRIEF DESCRIPTION OF THE DRAWINGS

The FIGURE illustrates addition of TMP to the reactor in production of ETBE. Isobutylene 1, TMP 2, ethanol 3, and recycle 12 are fed 4 to ethyl-tertiary-butyl ether reactor 5 containing ion exchange resin catalyst 6. The resulting reactor effluent is taken 7 to fractionator 8. Fractionator 8, heated indirectly at 9' and cooled indirectly at 9, provides overhead vapor 12 of an ethanol TMP azeotrope and unreacted isobutylene for recycle. The recycle 12 normally is condensed (not shown) for recovery and recycle. Bottoms 11 from fractionator 8 is a stream of substantially pure ETBE. Other details of the drawing will be described hereinafter in the detailed description of the invention.

REACTION OF ISOBUTYLENE WITH ETHANOL OR METHANOL

The conversion of the isobutylene (isobutene) to ETBE or MTBE by reaction with ethanol or methanol can be carried out in any suitable manner known in the art. A process for the production of ETBE and/or MTBE is disclosed in U.S. Pat. No. 2,480,940. A process for the production of MTBE is disclosed in "The New and Versatile Huls-Process to Produce the Octane Improving MTB", authored by Dr. Fritz Obenaus and Dr. Wilhelm Droste of Chemische Werke Huls AG, West Germany, American Institute of Chemical Engineers, Philadelphia (manuscript edition 1978).

OPERATING CONDITIONS

As is known to those skilled in the arts of fractionation, ETBE and MTBE manufacture, reactant ratios, space velocities combinations, and various temperature:pressure:reflux ratios, can be selected to effect the desired operational result.

The reaction usually employs an acid type ion exchange resin, such as a high molecular weight carbonaceous material containing sulfonate groups —$SO_3H$. Sulfonated resins of various types are available such as the sulfonated coals, phenol formaldehyde resins reacted with sulfuric acid, sulfonated resinous polymers of cumarone-indene with cyclopentadiene, strongly acidic cationic exchange resins such as sulfonated polystyrene resins, and others, under various commercial names. The catalyst can be employed in a particulate solid form of such as about 10 to 50 U.S. sieve, in a stirred liquid reaction system, employing about 0.5 to 50 percent dry weight of catalyst relative to liquid content of the reactor. Preferably, a fixed bed of particulate solid ion exchange resin catalyst, e.g. such as Amberlyst 15, is employed.

The reaction of the isobutylene with ethanol or methanol can be carried out under any suitable reaction conditions. The mole ratio of alcohol to isobutylene generally is in the range of about 0.05 to 10, preferably about 0.1 to 5, and still more usually about 1 to 1, at a temperature in the range of about 60° F. to 300° F., more usually about 120° F. to 200° F., employing a pressure sufficient to maintain the reactants substantially in the liquid state, typically in the range of about 30 to 300 psig. The liquid hourly space velocity, volumes of feed per volume of catalyst per hour, preferably is about 5 to 35.

Typical specific conditions:

| MTBE or ETBE Reactor: | |
|---|---|
| Temperature, °F. | 125 |
| Pressure, psig | to effect liquid state |
| Isobutylene/alcohol Mol Ratio | ~1:1 |
| Conversion, Vol. % | ~96 |
| Catalyst | |
| Amberlyst 15 | |
| (Rohm-Haas) | |
| Liquid Hourly Space Velocity | 5 |
| (Volume feed/Vol. Cat./Hour) | |
| Total Volume Percent of Feed of Isobutylene and Alcohol | about 25 |

The effluent from the reaction zone comprises isobutene, a small amount of unreacted alcohol (ethanol or methanol), and product ETME or MTBE. This reaction product stream is subjected to a separatory procedure for recovery of the ETBE or MTBE as bottoms in surprisingly pure form, as well as separation and recovery of the unreacted isobutene as overhead alone with the zeotropes as part of the overhead.

In the case of the production of ETBE, the azeotropic overhead is an azeotrope of ethanol/TMP, boiling at about 53° C. at standard temperature and pressure (STP) and at those conditions characterized as about 15.4 weight percent ethanol and 84.6 weight percent TMP.

In the case of the production of MTBE, the azeotropic overhead is an azeotrope of:

| methanol/F113 |
|---|
| BP. 39° C. (102° F.) at STP |
| methanol 6.4/F113 93.6, wt. % |
| or |
| methanol/TMB |
| BP. 45.6° C. (114° F.) at STP |
| methanol 21/TMP 79, wt. % |

CALCULATED EXAMPLE

The following Example further illustrates one aspect of my invention pertaining to the use of TMP in an improved ETBE process:

| (1) Feed Isobutylene, lbs/hr | | 90 |
|---|---|---|
| (2) Makeup 2-methylpentane, lbs/hr | | 0* |
| (3) Ethanol, lbs/hr | | 73.9 |
| (12) Recycle, lbs/hr | | 518.2 |
| Component | Lbs/Hr | |
| Ethanol | 8.2 | |
| Isobutylene | 10 | |
| 2-Methylpentane | 500 | |

*only as needed, after initial charge, to maintain sufficiency for azeotropic distillation.

| (6) Reactor Conditions | |
|---|---|
| Catalyst | Amberlyst 15 |
| Ethanol/Isobutylene Mol. Ratio | 1:1 |
| Inlet Temperature, °F. | 120 |
| Conversion, Mol. % | 90 |
| Pressure | To maintain liquid phase state |
| LHSV, vol. feed/vol. cat/hr | 6 |
| (7) Reactor Effluent, Lbs/Hr, | 682.1 |
| Component | Lbs/Hr |
| Ethanol | 8.2 |
| Isobutylene | 10 |
| 2-Methylpentane | 500 |
| ETBE | 163.9 |
| Fractionator: | |
| Temperatures, °F. | |
| Top | 127 |
| Bottom | 140–144 |
| Pressure, psig | 1 atmosphere |

Of course, in the aspect of my invention(s) pertaining to the use of TMP or F113 in an improved MTBE recovery process, similar calculations can be readily made by those skilled in the art from the data I have given relative to operating conditions and the respective azeotropes.

In feeding the TMP or F113 to either system, the TMP or F113 azeotroping agent effects azeotropic distillation of alcohol from the alcohol-containing ether-reactor stream. This is important to give a clean stripping of alcohol from the ether in fractionation, producing substantially pure ether bottom stream, of ETBE or MTBE, from the fractionator. The overhead, of course, generally additionally contains unreacted isobutene which can be readily recycled to the reactor. The TMP or F113 in the system merely recycles, and the level (content) thereof readily checked and augmented as necessary.

The disclosure, including data, has illustrated the value and effectiveness of my invention. The knowledge and background of the field of the invention, of general principles of chemical engineering and of other applicable sciences and the exemplary data presented, have formed the bases to which the broad description of the invention, including the ranges of conditions have been developed, as well as the bases for my claims here appended.

I claim:

1. A process for the production of MTBE which comprises reacting methanol and isobutene under reaction conditions to form a methanol-containing methyl-tertiary butyl ether reactor effluent stream comprising unreacted isobutylene, unreacted methanol, and product methyl tertiary butyl ether, and fractionating said MTBE reactor effluent stream in admixture with an azeotroping component selected from the group consisting of 2-methylpentane and 1,1,2-trichloro-1,2,2-trifluoroethane, thereby taking unreacted methanol as an azeotropic overhead stream, wherein said overhead stream further contains unreacted isobutylene, and taking as product methyl tertiary butyl ether as bottoms.

2. The process according to claim 1 wherein said azeotroping agent 2-methylpentane or 1,1,2-trichloro-1,2,2-trifluoroethane is added prior to the reacting step to form said reactor effluent stream, and becomes a component of said reactor effluent stream.

3. The process according to claim 1 wherein said azeotroping agent 2-methylpentane or 1,1,2-trichloro-1,2,2-trifluoroethane is added to said reactor effluent stream.

4. The process according to claim 1, 2, or 3 wherein said overhead stream is recycled at least in part to said reacting step.

5. The process of claim 1, 2, or 3 wherein said azeotroping component is said 2-methylpentane.

6. The process of claim 1, 2, or 3 wherein said azeotroping component is 1,1,2-trichloro-1,2,2-trifluoroethane.

7. The process of claim 4 wherein said azeotroping component is said 2-methylpentane.

8. The process of claim 4 wherein said azeotroping component is 1,1,2-trichloro-1,2,2-trifluoroethane.

9. A process for the production of ETBE which comprises reacting ethanol and isobutene under ether forming reaction conditions to form an ethyl-tertiary-butyl ether reactor effluent stream comprising unreacted isobutylene, unreacted ethanol, and product ethyl tertiary butyl ether, and fractionating said ethyl-tertiary-butyl ether reactor effluent stream in admixture with 2-methylpentane, thereby taking unreacted ethanol as an ethanol/2-methylpentane azeotropic overhead stream, wherein said overhead stream further contains unreacted isobutylene, and taking product ethyl-tertiary-butyl ether as bottoms.

10. The process according to claim 9 wherein said 2-methylpentane is added prior to said reacting step, and is a component of said reactor effluent.

11. The process according to claim 9, wherein said 2-methylpentane is added to said reactor effluent prior to said fractionating step.

12. The process according to claim 9, 10, or 11 wherein said overhead stream is recycled at least in part to said reacting step.

* * * * *